United States Patent
Langevin et al.

(10) Patent No.: US 7,642,249 B2
(45) Date of Patent: *Jan. 5, 2010

(54) DIHYDROGEN PHOSPHATE SALT OF A PROSTAGLANDIN D2 RECEPTOR ANTAGONIST

(75) Inventors: Beverly Langevin, Stewartsville, NJ (US); Edward Orton, Berkley Heights, NJ (US); Daniel Sherer, Berkley Heights, NJ (US)

(73) Assignee: Aventis Pharmaceuticals Inc., Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/101,282

(22) Filed: Apr. 11, 2008

(65) Prior Publication Data

US 2008/0194600 A1    Aug. 14, 2008

Related U.S. Application Data

(63) Continuation of application No. PCT/US2006/039901, filed on Oct. 12, 2006.

(60) Provisional application No. 60/726,290, filed on Oct. 13, 2005.

(51) Int. Cl.
*C07D 239/46* (2006.01)
*A61K 31/505* (2006.01)

(52) U.S. Cl. .................. 514/86; 514/274; 544/243; 544/317

(58) Field of Classification Search .............. 544/243, 544/317; 514/86, 274
See application file for complete search history.

(56) References Cited

U.S. PATENT DOCUMENTS

| | | | |
|---|---|---|---|
| 7,078,401 B2 | 7/2006 | Bley et al. | |
| 2003/0199526 A1 | 10/2003 | Choquette et al. | |
| 2007/0244131 A1 | 10/2007 | Lim | |
| 2007/0265291 A1 | 11/2007 | Harris | |

OTHER PUBLICATIONS

Kabashima et al., The DP receptor, allergic inflammation and asthma, Prostaglandins, Leukotrienes and Essential Fatty Acids, 69, pp. 187-194 (2003).*

* cited by examiner

*Primary Examiner*—Deepak Rao
(74) *Attorney, Agent, or Firm*—Ronald G. Ort; Jiang Lin

(57) ABSTRACT

The present invention is directed to dihydrogen phosphate salt 2-(3-{6-[2-(2,4-dichloro-phenyl)-ethylamino]-2-methoxy-pyrimidin-4-yl}-phenyl)-2-methyl-propionic acid of Formula (III),

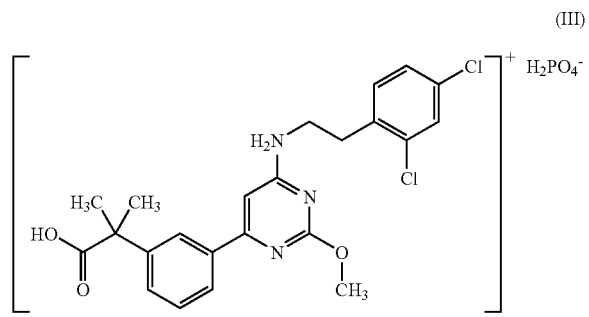

a pharmaceutical composition comprising a pharmaceutically effective amount of the compound of Formula (III), and a pharmaceutically acceptable carrier; and a method of treating a patient suffering from a PGD2-mediated disorder including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like, by administering to said patient a pharmaceutically effective amount of the compound of Formula (III).

3 Claims, 12 Drawing Sheets

FIGURE 2

| d value Angstrom | Intensity Counts per second | Intensity % |
|---|---|---|
| 14.8569 | 432 | 100 |
| 8.99176 | 20 | 4.6 |
| 7.98188 | 16 | 3.7 |
| 7.44027 | 140 | 32.4 |
| 6.62368 | 16 | 3.7 |
| 6.4151 | 129 | 29.9 |
| 6.1624 | 30 | 6.9 |
| 5.99021 | 56 | 13 |
| 5.66647 | 88 | 20.4 |
| 5.02924 | 43 | 10 |
| 4.63324 | 33 | 7.6 |
| 4.47588 | 52 | 12 |
| 4.38059 | 43 | 10 |
| 4.24939 | 62 | 14.4 |
| 4.00502 | 54 | 12.5 |
| 3.87391 | 97 | 22.5 |
| 3.80718 | 71 | 16.4 |
| 3.65039 | 31 | 7.2 |
| 3.60586 | 32 | 7.4 |
| 3.40887 | 102 | 23.6 |
| 3.34156 | 41 | 9.5 |
| 3.21265 | 54 | 12.5 |
| 3.11305 | 29 | 6.7 |
| 3.0758 | 22.6 | 5.2 |
| 2.96596 | 36 | 8.3 |
| 2.90645 | 35 | 8.1 |

| Thermal Event | The Dihydrogen Phosphate Salt |
|---|---|
| Melting Point | 219°C |

|  | Sample | Change In Mass (%) | | |
|---|---|---|---|---|
|  | RH (%) | Sorption | Desorption | Hysteresis |
| Cycle 1 | 0.1 | 0.0000 | 0.0133 | |
|  | 8.6 | 0.0340 | 0.0464 | 0.0124 |
|  | 19.2 | 0.0572 | 0.0730 | 0.0158 |
|  | 28.7 | 0.0879 | 0.1004 | 0.0124 |
|  | 38.2 | 0.1169 | 0.1335 | 0.0166 |
|  | 48.3 | 0.1518 | 0.1609 | 0.0091 |
|  | 57.7 | 0.1932 | 0.2123 | 0.0191 |
|  | 66.9 | 0.2447 | 0.2679 | 0.0232 |
|  | 75.9 | 0.3118 | 0.3400 | 0.0282 |
|  | 85.2 | 0.4404 | 0.4644 | 0.0241 |
|  | 94.1 | 0.9040 | 0.9040 | |
| Cycle 2 | 0.1 | 0.0133 | 0.0182 | |
|  | 8.9 | 0.0440 | 0.0531 | 0.0091 |
|  | 19.4 | 0.0672 | 0.0804 | 0.0133 |
|  | 28.8 | 0.0995 | 0.1086 | 0.0091 |
|  | 38.4 | 0.1310 | 0.1410 | 0.0100 |
|  | 48.4 | 0.1659 | 0.1758 | 0.0100 |
|  | 57.8 | 0.2123 | 0.2272 | 0.0149 |
|  | 66.9 | 0.2629 | 0.2828 | 0.0199 |
|  | 75.8 | 0.3326 | 0.3541 | 0.0216 |
|  | 85.2 | 0.4611 | 0.4802 | 0.0191 |
|  | 94.0 | 0.9463 | 0.9463 | |

| Change in Mass (%) | Sample RH (%) |
|---|---|
| 0.000 | 1.14 |
| -0.001 | 2.17 |
| 0.008 | 5.05 |
| 0.026 | 9.90 |
| 0.054 | 19.94 |
| 0.079 | 29.92 |
| 0.102 | 39.92 |
| 0.124 | 49.86 |
| 0.146 | 59.83 |
| 0.170 | 69.89 |
| 0.196 | 79.69 |
| 0.234 | 89.51 |
| 0.263 | 94.72 |
| 0.245 | 89.77 |
| 0.215 | 79.96 |
| 0.191 | 70.01 |
| 0.168 | 60.03 |
| 0.145 | 50.15 |
| 0.124 | 40.04 |
| 0.104 | 30.17 |
| 0.083 | 19.81 |
| 0.056 | 10.26 |
| 0.039 | 4.87 |
| 0.022 | 2.07 |

| Peak Position (cm$^{-1}$) |
|---|
| 3246.33 |
| 2943.13 |
| 1729.41 |
| 1654.53 |
| 1625.97 |
| 1595.66 |
| 1535.18 |
| 1494.85 |
| 1471.73 |
| 1362.52 |
| 1251.90 |
| 1107.05 |
| 1051.19 |
| 1027.20 |
| 945.09 |
| 892.45 |
| 864.26 |
| 852.33 |
| 823.94 |
| 803.36 |
| 768.17 |
| 749.19 |
| 695.68 |
| 687.27 |
| 668.53 |

DIHYDROGEN PHOSPHATE SALT OF A PROSTAGLANDIN D2 RECEPTOR ANTAGONIST

This application is a continuation of PCT/US2006/039901 filed Oct. 12, 2006 which claims benefit of U.S. Provisional Application No. 60/726,290 filed Oct. 13, 2005.

FIELD OF THE INVENTION

Large-scale manufacturing of a pharmaceutical composition may pose many challenges to the chemist and chemical engineer. While many of these challenges relate to the handling of large quantities of reagents and control of large-scale reactions, the handling of the final product poses special challenges linked to the nature of the final active product itself. Not only must the product be prepared in high yield, be stable, and capable of ready isolation, the product must possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term formulation. Each of these steps may be impacted by various environmental conditions of temperature and humidity.

The pharmaceutically active substance used to prepare the pharmaceutical compositions should be as pure as possible and its chemical stability on long-term storage must be guaranteed under various environmental conditions. This is absolutely essential to prevent the appearance of undesirable degradation products in pharmaceutical compositions. These degradation products may be potentially toxic, or result simply in reducing the potency of the composition.

A primary concern for the large-scale manufacture of pharmaceutical compounds is that the active substance should maintain a polymorphic stability during its handling to ensure consistent processing parameters and pharmaceutical quality. Depending on the stability characteristics of a pharmaceutical compound it may be subject to undergoing changes during manufacture and/or storage potentially resulting in quality control problems, and formulation issues. Such a change may affect the reproducibility of the manufacturing process and thus lead to final formulations which may not meet the high quality and stringent requirements imposed by regulatory agencies on formulations of pharmaceutical compositions. With the aforesaid in mind, it should be generally borne in mind that at least the selection of a pharmaceutical compound that has improved physical stability characteristics can provide for significant advantages over less stable forms of the same compound.

The present invention is directed to the dihydrogen phosphate salt of a pharmacologically active prostaglandin D2 receptor antagonist having highly preferred physical properties. The compound is useful as a DP antagonist for treating a patient suffering from, or subject to, PGD2 mediated pathological (diseases) conditions, including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like.

BACKGROUND OF THE INVENTION

Local allergen challenge in patients with allergic rhinitis, bronchial asthma, allergic conjunctivitis and atopic dermatitis has been shown to result in rapid elevation of prostaglandin D2 "(PGD2)" levels in nasal and bronchial lavage fluids, tears and skin chamber fluids. PGD2 has many inflammatory actions, such as increasing vascular permeability in the conjunctiva and skin, increasing nasal airway resistance, airway narrowing and eosinophil infiltration into the conjunctiva and trachea.

PGD2 is the major cyclooxygenase product of arachidonic acid produced from mast cells on immunological challenge [Lewis, R A, Soter N A, Diamond P T, Austen K F, Oates J A, Roberts L J II, Prostaglandin D2 generation after activation of rat and human mast cells with anti-IgE, *J. Immunol.* 129, 1627-1631, 1982]. Activated mast cells, a major source of PGD2, are one of the key players in driving the allergic response in conditions such as asthma, allergic rhinitis, allergic conjunctivitis, allergic dermatitis and other diseases [Brightling C E, Bradding P, Pavord I D, Wardlaw A J, New Insights into the role of the mast cell in asthma, *Clin. Exp. Allergy* 33, 550-556, 2003].

Many of the actions of PGD2 are mediated through its action on the D-type prostaglandin ("DP") receptor, a G protein-coupled receptor expressed on epithelium and smooth muscle. In asthma, the respiratory epithelium has long been recognized as a key source of inflammatory cytokines and chemokines that drive the progression of the disease [Holgate S, Lackie P, Wilson S, Roche W, Davies D, Bronchial Epithelium as a Key Regulator of Airway Allergen Sensitization and Remodelling in Asthma, *Am J Respir Crit Care Med.* 162, 113-117, 2000]. In an experimental mouse model of asthma, the DP receptor is dramatically up-regulated on airway epithelium on antigen challenge [Matsuoka T, Hirata M, Tanaka H, Takahashi Y, Murata T, Kabashima K, Sugimoto Y, Kobayashi T, Ushikubi F, Aze Y, Eguchi N, Urade Y, Yoshida N, Kimura K, Mizoguchi A, Honda Y, Nagai H, Narumiya S, prostaglandin D2 as a mediator of allergic asthma, *Science* 287, 2013-2017, 2000]. In knockout mice, lacking the DP receptor, there is a marked reduction in airway hyperreactivity and chronic inflammation, two of the cardinal features of human asthma [Matsuoka T, Hirata M, Tanaka H, Takahashi Y, Murata T, Kabashima K, Sugimoto Y, Kobayashi T, Ushikubi F, Aze Y, Eguchi N, Urade Y, Yoshida N, Kimura K, Mizoguchi A, Honda Y, Nagai H, Narumiya S, Prostaglandin D2 as a mediator of allergic asthma, *Science* 287, 2013-2017, 2000].

The DP receptor is also thought to be involved in human allergic rhinitis, a frequent allergic disease that is characterized by the symptoms of sneezing, itching, rhinorrhea and nasal congestion. Local administration of PGD2 to the nose causes a dose dependent increase in nasal congestion [Doyle W J, Boehm S, Skoner D P, Physiologic responses to intranasal dose-response challenges with histamine, methacholine, bradykinin, and prostaglandin in adult volunteers with and without nasal allergy, *J Allergy Clin Immunol.* 86(6 Pt 1), 924-35, 1990].

DP receptor antagonists have been shown to reduce airway inflammation in a guinea pig experimental asthma model [Arimura A, Yasui K, Kishino J, Asanuma F, Hasegawa H, Kakudo S, Ohtani M, Arita H, Prevention of allergic inflammation by a novel prostaglandin receptor antagonist, S-5751,

*J Pharmacol Exp Ther.* 298(2), 411-9, 2001]. PGD2, therefore appears to act on the DP receptor and plays an important role in elicitation of certain key features of allergic asthma.

DP antagonists have been shown to be effective at alleviating the symptoms of allergic rhinitis in multiple species, and more specifically have been shown to inhibit the antigen-induced nasal congestion, the most manifest symptom of allergic rhinitis [Jones, T. R., Savoie, C., Robichaud, A., Sturino, C., Scheigetz, J., Lachance, N., Roy, B., Boyd, M., Abraham, W., Studies with a DP receptor antagonist in sheep and guinea pig models of allergic rhinitis, *Am. J. Resp. Crit. Care Med.* 167, A218, 2003; and Arimura A, Yasui K, Kishino J, Asanuma F, Hasegawa H, Kakudo S, Ohtani M, Arita H, Prevention of allergic inflammation by a novel prostaglandin receptor antagonist, S-5751. *J. Pharmacol. Exp. Ther.* 298(2), 411-9, 2001].

DP antagonists are also effective in experimental models of allergic conjunctivitis and allergic dermatitis [Arimura A, Yasui K, Kishino J, Asanuma F, Hasegawa H, Kakudo S, Ohtani M, Arita H, Prevention of allergic inflammation by a novel prostaglandin receptor antagonist, S-5751. *J. Pharmacol. Exp. Ther.* 298(2), 411-9, 2001; and Torisu K, Kobayashi K, Iwahashi M, Nakai Y, Onoda T, Nagase T, Sugimoto I, Okada Y, Matsumoto R, Nanbu F, Ohuchida S, Nakai H, Toda M, Discovery of a new class of potent, selective, and orally active prostaglandin D₂ receptor antagonists, *Bioorg. & Med. Chem.* 12, 5361-5378, 2004].

Patent application WO 2006044732 (hereinafter the '732 publication), hereby incorporated by reference, discloses pyrimidines that have valuable pharmaceutical properties including, in particular, the ability to associate with and regulate the DP receptor. The '732 publication discloses pyrimidines of Formula (I),

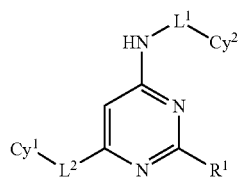

(I)

their preparation, pharmaceutical compositions containing these compounds, and their pharmaceutical use in the treatment of disease states capable of being modulated by the inhibition of the prostaglandin D2 receptor. Furthermore, the '732 publication specifically discloses and claims 2-(3-{6-[2-(2,4-dichloro-phenyl)-ethylamino]-2-methoxy-pyrimidin-4-yl}-phenyl)-2-methyl-propionic acid (hereinafter "the free form"). The '732 publication also provides a general description of a wide variety of acid addition salts and base addition salts of compounds according to the invention, and assorted working examples limited to the preparation of hydrochloride salts and sodium salts. More specifically the hydrochloride salt and sodium salt of 2-(3-{6-[2-(2,4-dichloro-phenyl)-ethylamino]-2-methoxy-pyrimidin-4-yl}-phenyl)-2-methyl-propionic acid are disclosed. The '732 publication, however, does not specifically disclose a dihydrogen phosphate salt of 2-(3-{6-[2-(2,4-dichloro-phenyl)-ethylamino]-2-methoxy-pyrimidin-4-yl}-phenyl)-2-methyl-propionic acid.

SUMMARY OF THE INVENTION

The present invention is directed to the dihydrogen phosphate salt of 2-(3-{6-[2-(2,4-dichloro-phenyl)-ethylamino]-2-methoxy-pyrimidin-4-yl}-phenyl)-2-methyl-propionic acid of Formula (III) (hereinafter "the dihydrogen phosphate salt").

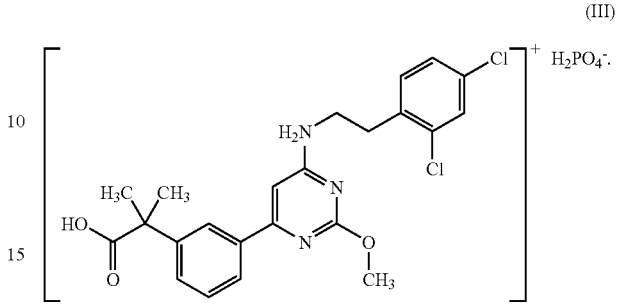

(III)

Another aspect of the present invention is a pharmaceutical composition, comprising a pharmaceutically effective amount of the dihydrogen phosphate salt.

Another aspect of the present invention is a method for treating a patient suffering from a PGD2-mediated disorder including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like, by administering to the patient a pharmaceutically effective amount of the dihydrogen phosphate salt of 2-(3-{6-[2-(2,4-dichloro-phenyl)-ethylamino]-2-methoxy-pyrimidin-4-yl}-phenyl)-2-methyl-propionic acid.

The present invention is more fully discussed with the aid of the following figures and detailed description below.

BRIEF DESCRIPTION OF THE DRAWINGS

FIG. 2 is the corresponding Table of XRPD d-Spacings and Relative Intensities for the powder X-ray diffractogram in FIG. 1 of the dihydrogen phosphate salt.

DETAILED DESCRIPTION OF THE INVENTION

Definitions and Abbreviations

Figure 1:
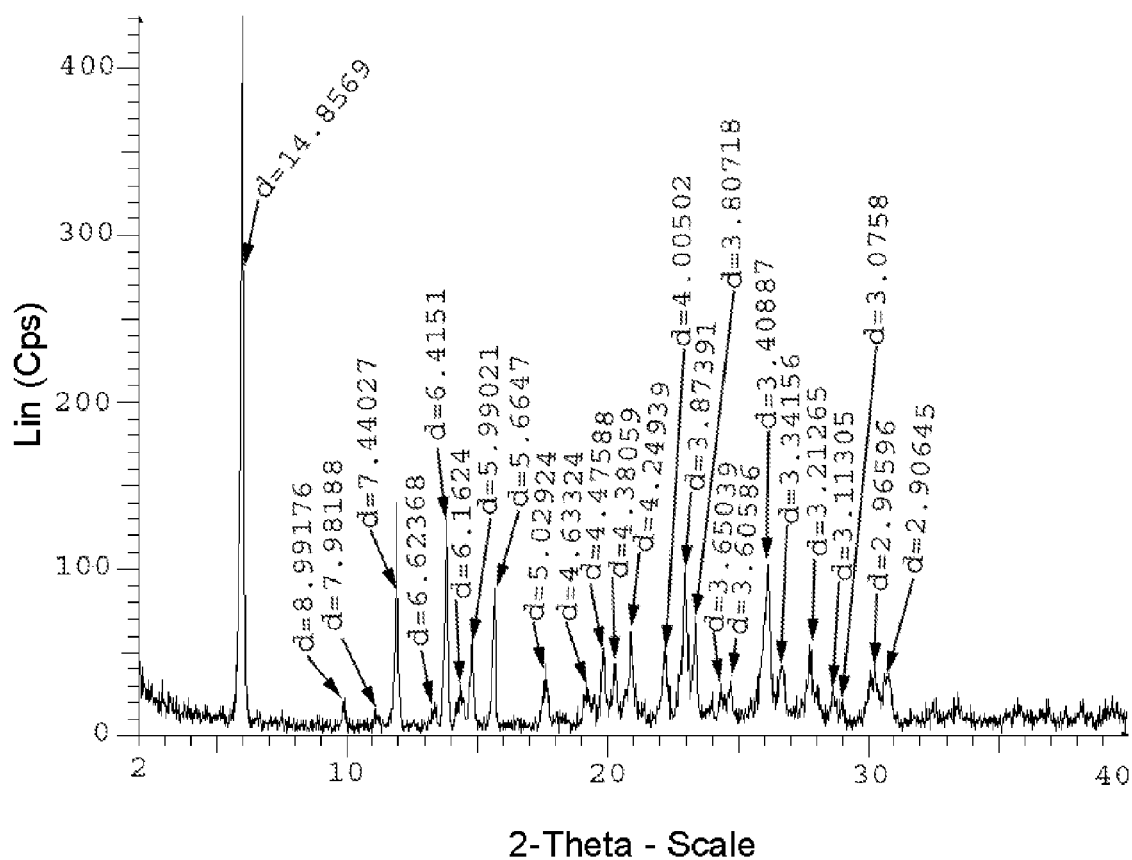
FIG. 1 is a X-ray Powder Diffraction pattern (XRPD) of the dihydrogen phosphate salt.
Figure 3:
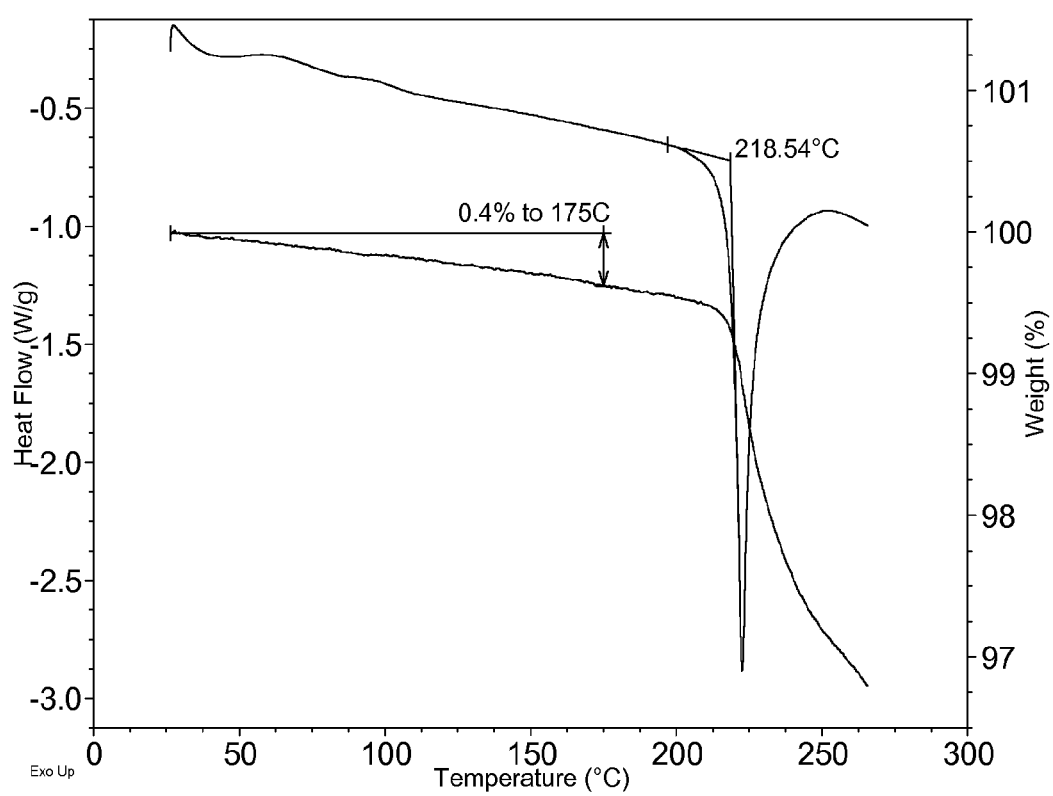
FIG. 3 is a differential scanning calorimeter-thermal gravimetric analyzer (DSC-TGA) thermogram of the dihydrogen phosphate salt. The TGA data shows a total weight loss of approximately 0.4% from room temperature to 175° C. The DSC contains only the melt of the crystalline phase. Decomposition of the molecule begins at the melting temperature.
Figure 4:
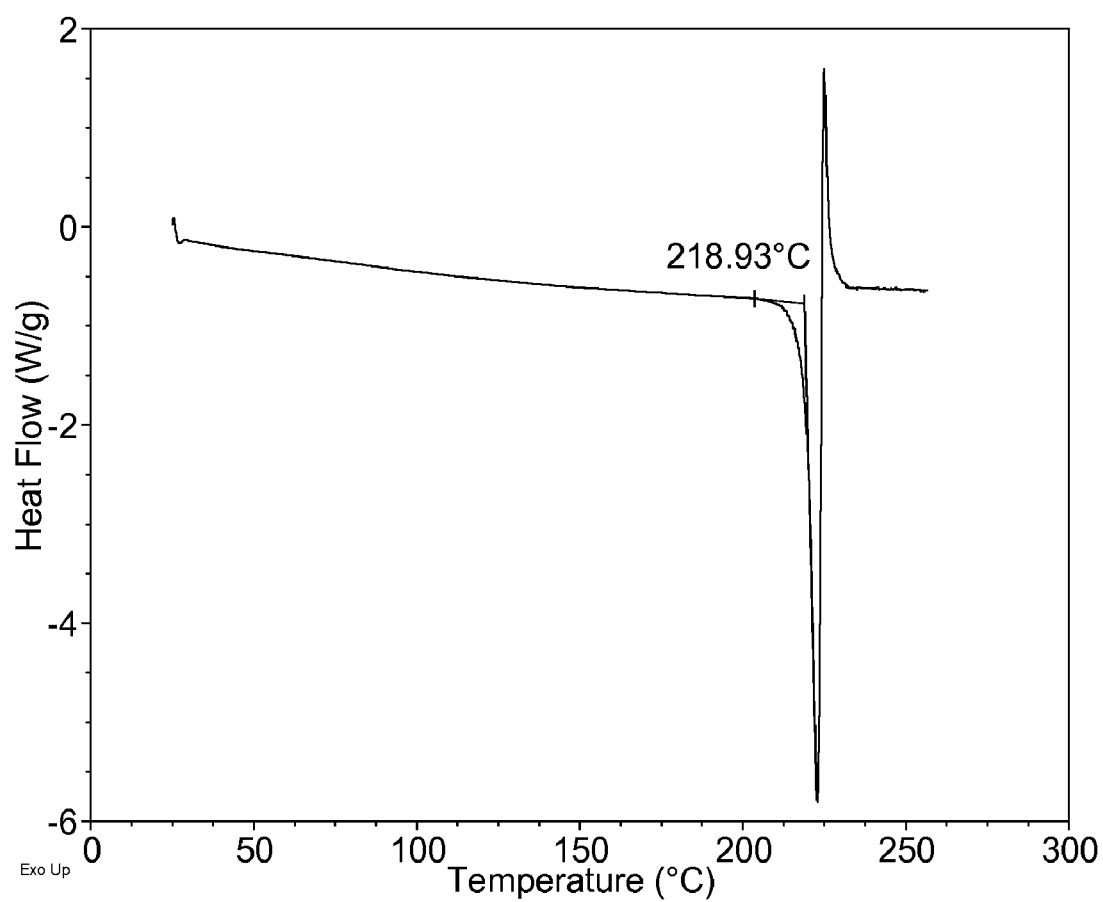
FIG. 4 is a DSC thermogram of the dihydrogen phosphate salt. The melt is the only thermal event observed in the thermogram at onset 219° C.
Figure 5:
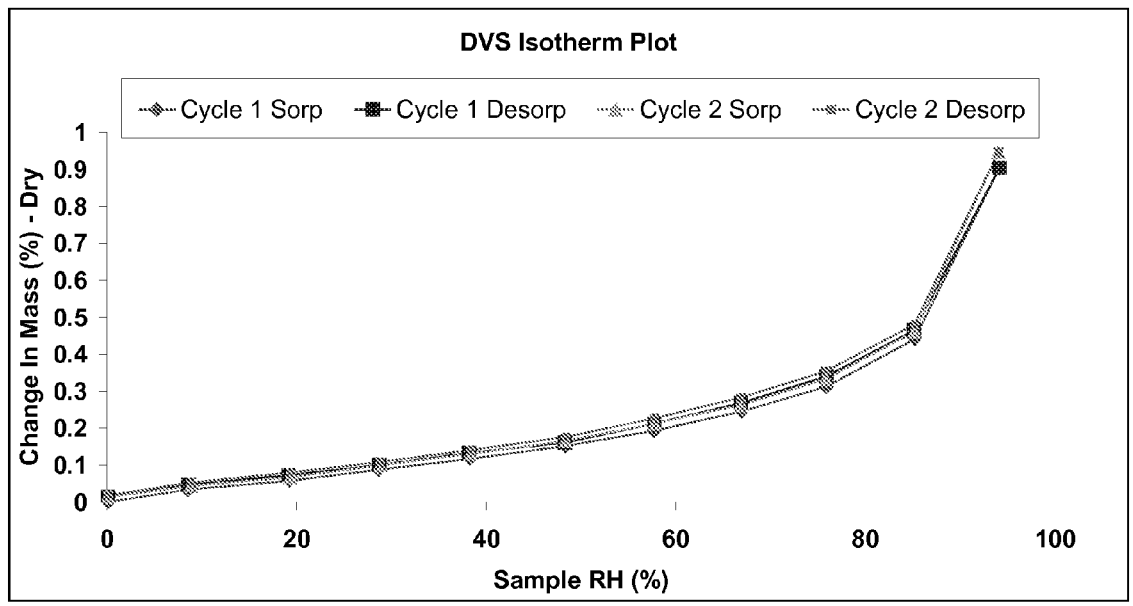
FIG. 5 shows a Dynamic Vapor Sorption Analyzer (DVS) Hygroscopicity Isotherm plot of the dihydrogen phosphate salt and the corresponding Table Water Sorption Profile. The date show weight gain during the sorption of ~0.9% at 94% relative humidity (RH) with little hysteresis suggesting loosely bound surface water sorption.
Figure 6:
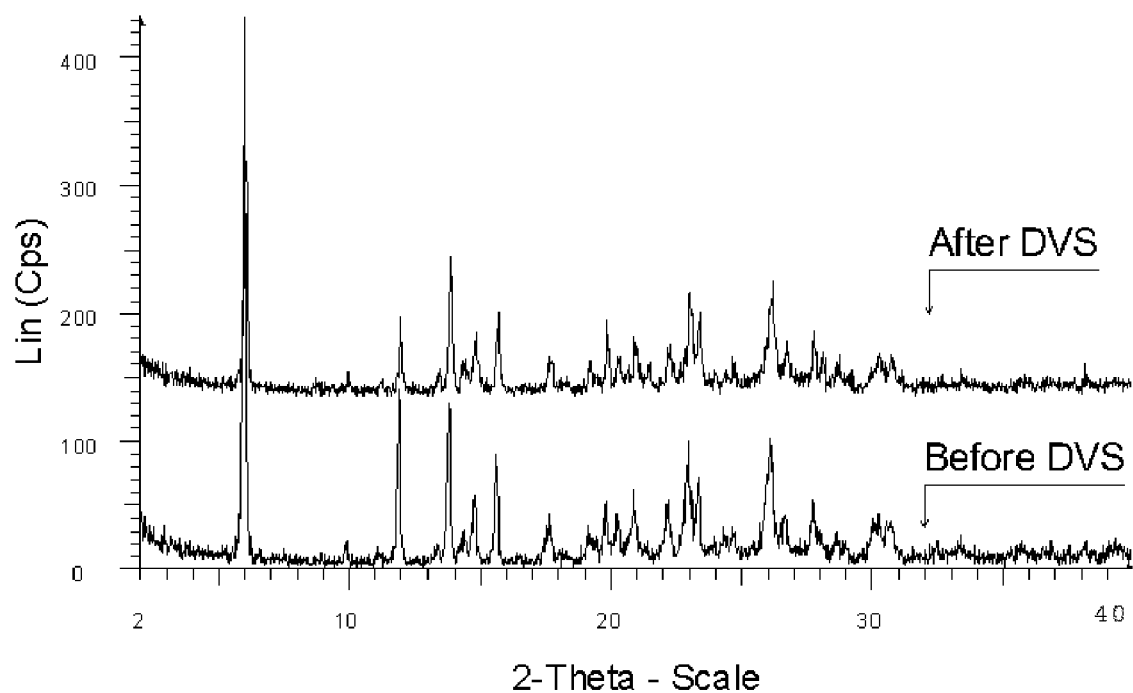
FIG. 6 shows the XRPD patterns of the dihydrogen phosphate salt before and after DVS. The specimen is prepared, and the analysis starts within 2 minutes of removal from the DVS where it has been allowed to stand at 0% RH for ~12 hours. The data show little change in intensity and d-spacing as a result of DVS experiment, indicating that no detectable changes in the crystalline structure occurred.
Figure 7:
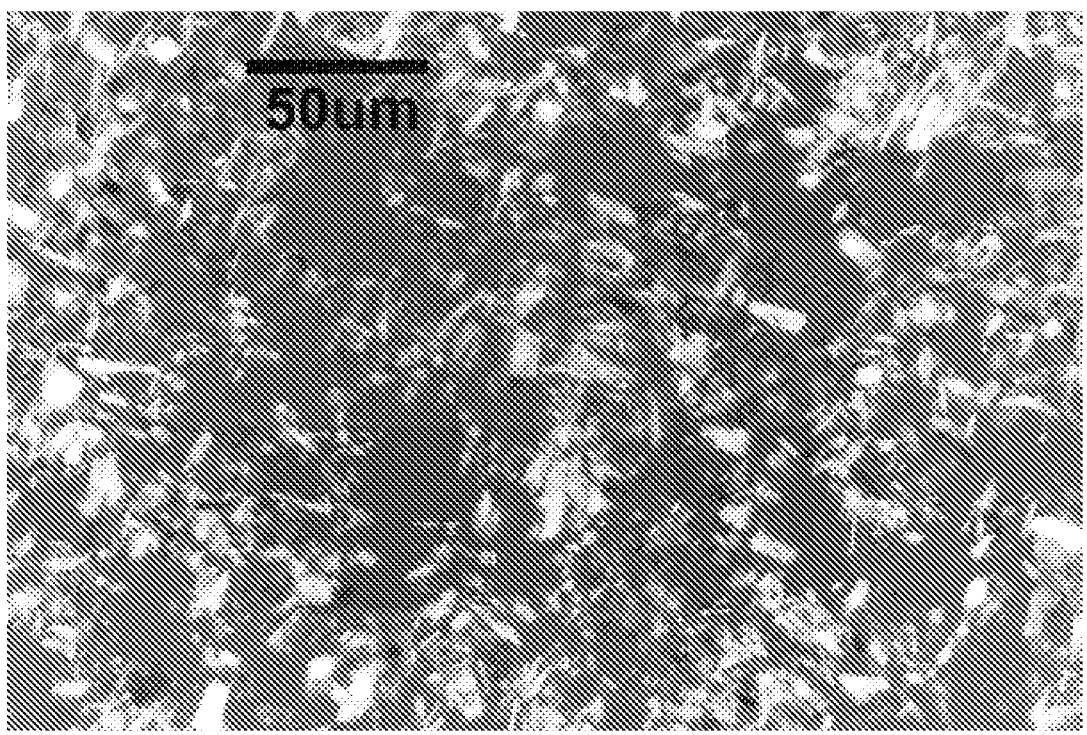
FIG. 7 shows the photomicrograph of the dihydrogen phosphate salt. The lot consists primarily of rod and needles shaped particles up to about 30 microns in length.

As used above, and throughout the description of the invention, the following abbreviations, unless otherwise indicated, shall be understood to have the following meanings:

DMSO Dimethyl sulfoxide
cAMP cyclic adenosine monophosphate
IBMX 3-isobutyl-1-methylxanthine
SPA Scintillation Proximity Assay
ATTC American Type Culture Collection
MEM Minimal Essential Medium
FBS Fetal Bovine Serum
CPM Counts Per Minute As used above, and throughout the description of the invention, the following terms, unless otherwise indicated, shall be understood to have the following meanings.

"Treating" or "treatment" means prevention, partial alleviation, or cure of the disease. The compound and composition of this invention are useful in treating a PGD2-mediated disorder, including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like, by administering to said patient a pharmaceutically effective amount of the compound according to Formula (III).

"Patient" includes both human and other mammals.

"Pharmaceutically effective amount" is meant to describe an amount of a compound, composition, medicament or other active ingredient effective in producing the desired therapeutic effect.

PARTICULAR EMBODIMENTS OF THE INVENTION

One particular embodiment of the invention is a compound of formula (III) in a crystalline form.

The compound of the invention exhibits prostaglandin D2 receptor antagonist activity and is a useful pharmacological acting agent. Accordingly, it is incorporated into pharmaceutical compositions and used in the treatment of patients suffering from certain medical disorders.

The compound of the invention is an antagonist of the prostaglandin D2 receptor, according to tests described in the literature and described in pharmacological testing section hereinafter, and which tests results are believed to correlate to pharmacological activity in humans and other mammals. Thus, in a further embodiment, the present invention provides the compound of the invention and compositions containing the compound of the invention for use in the treatment of a patient suffering from, or subject to, conditions, which can be ameliorated by the administration of a PGD2 antagonist. For example, the compound of the present invention could therefore be useful in the treatment of a variety of PGD2-mediated disorders including, but not limited to, allergic disease (such as allergic rhinitis, allergic conjunctivitis, atopic dermatitis, bronchial asthma and food allergy), systemic mastocytosis, disorders accompanied by systemic mast cell activation, anaphylaxis shock, bronchoconstriction, bronchitis, urticaria, eczema, diseases accompanied by itch (such as atopic dermatitis and urticaria), diseases (such as cataract, retinal detachment, inflammation, infection and sleeping disorders) which is generated secondarily as a result of behavior accompanied by itch (such as scratching and beating), inflammation, chronic obstructive pulmonary diseases, ischemic reperfusion injury, cerebrovascular accident, chronic rheumatoid arthritis, pleurisy, ulcerative colitis and the like.

One particular embodiment of the therapeutic methods of the present invention is the treating of allergic rhinitis.

Another particular embodiment of the therapeutic methods of the present invention is the treating of bronchial asthma.

Another particular embodiment of the therapeutic methods of the present invention is the treating of COPD.

Another particular embodiment of the therapeutic methods of the present invention is the treating of allergic conjunctivitis.

Another particular embodiment of the therapeutic methods of the present invention is the treating of allergic dermatitis.

References herein to treatment should be understood to include prophylactic therapy as well as treatment of established conditions.

The compound of the present invention is further useful in treatments involving a combination therapy with at least one of a:

(i) antihistamines, such as fexofenadine, desloratadine, loratadine and citirizine, for the treatment of allergic rhinitis;
(ii) leukotriene antagonists, such as montelukast and zafirulast, for the treatment of allergic rhinitis, COPD, allergic dermatitis, allergic conjunctivitis, etc—please specifically refer to the claims in WO 01/78697 A2;
(iii) beta agonists, such as albuterol, salbuterol and terbutaline, for the treatment of asthma, COPD, allergic dermatitis, allergic conjunctivitis, etc;
(iv) antihistamines, such as fexofenadine, loratadine and citirizine, for the treatment of asthma, COPD, allergic dermatitis, allergic conjunctivitis, etc;
(v) PDE4 (Phosphodiesterase 4) inhibitors, such as roflumilast and cilomilast, for the treatment of asthma, COPD, allergic dermatitis, allergic conjunctivitis, etc; or
(vi) with TP (Thromboxane A2 receptor) or CrTh2 (chemoattractant receptor-homologous molecule expressed on Th2 cells) antagonists, such as Ramatrobran (BAY-u3405), for the treatment of COPD, allergic dermatitis, allergic conjunctivitis, etc.

The present invention also includes within its scope a pharmaceutical composition comprising a pharmaceutically effective amount of the compound of the invention in admixture with a pharmaceutically acceptable carrier.

In practice, the compound of the present invention may be administered in pharmaceutically acceptable dosage form to humans and other mammals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the particular route may vary with for example the physiological condition of the recipient.

"Pharmaceutically acceptable dosage forms" refers to dosage forms of the compound of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for the compound of the invention to be administered in the form of a pharmaceutical composition.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride, and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates. Exemplary lubricants include magnesium stearate, sodium lauryl sulfate, talc, as well as high molecular weight polyethylene glycols.

The choice of pharmaceutical acceptable carrier is generally determined in accordance with the chemical properties of the active compound such as solubility, the particular mode of administration and the provisions to be observed in pharmaceutical practice.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of the compound of the invention is solid form, for example capsules, tablets, pills, powders, dragées or granules. In such solid dosage forms, the compound of the invention is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound of the invention in a certain part of the intestinal tract in a delayed manner.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compound can be microencapsulated in, or attached to, a slow release or targeted delivery systems such as a biocompatible, biodegradable polymer matrices (e.g., poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria-retaining filter, or by incorporating sterilizing agents in the form of sterile solid compositions which can be dissolved in sterile water, or some other sterile injectable medium immediately before use.

"Liquid dosage form" means the dose of the active compound to be administered to the patient is in liquid form, for example, pharmaceutically acceptable emulsions, solutions, suspensions, syrups and elixirs. In addition to the active compound, the liquid dosage forms may contain inert diluents commonly used in the art, such solvents, solubilizing agents and emulsifiers.

When aqueous suspensions are used they can contain emulsifying agents or agents which facilitate suspension.

Pharmaceutical compositions suitable for topical administration means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients, in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with, or without, stabilizer(s) make up the emulsifying wax, and together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as, propylene glycol, butane 1,3-diol, mannitol, sorbitol, glycerol and polyethylene glycol (including PEG 400) and mixtures thereof. The topical formulations may desirably include a compound that enhances absorption, or penetration of the active ingredient through the skin, or other affected areas.

The choice of suitable oils or fats for a composition is based on achieving the desired properties. Thus a cream should particularly be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations mean formulations that are in a form suitable to be administered rectally or vaginally to a patient and containing at least one compound of the invention. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical composition administered by injection may be by transmuscular, intravenous, intraperitoneal, and/or subcutaneous injection. The compositions of the present invention are formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and antioxidants, buffers, bacteriostats and solutes which render the formulation isotonic, and have a suitably adjusted pH, with the blood of the intended recipient.

Pharmaceutical composition of the present invention suitable for nasal or inhalational administration means compositions that are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Inhalational therapy is readily administered by metered dose inhalers or any suitable dry powder inhaler, such as the Eclipse, Spinhaler®, or Ultrahaler® as described in patent application WO2004/026380, and U.S. Pat. No. 5,176,132.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, the route of administration, the desired duration of treatment, the etiology and severity of the disease, the patient's condition, weight, sex, diet and age, the type and potency of each active ingredient, rates of absorption, metabolism and/or excretion and other factors.

Total daily dose of the compound of this invention administered to a patient in single or divided doses may be in amounts, for example, of from about 0.001 to about 100 mg/kg body weight daily and particularly 0.01 to 10 mg/kg/day. For example, in an adult, the doses are generally from about 0.01 to about 100, particularly about 0.01 to about 10, mg/kg body weight per day by inhalation, from about 0.01 to about 100, particularly 0.1 to 70, more especially 0.5 to 10, mg/kg body weight per day by oral administration, and from about 0.01 to about 50, particularly 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much lower maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the pharmaceutically active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compound of the invention is analyzed by the following analytical methods.

High Pressure Liquid Chromatography—Mass Spectrometry (LCMS)

LCMS experiments to determine retention times ($R_T$) and associated mass ions are performed using the following method. Mass Spectra (MS) are recorded using a Micromass LCT mass spectrometer. The method is positive electrospray ionization, scanning mass m/z from 100 to 1000. Liquid chromatography is performed on a Hewlett Packard 1100 Series Binary Pump & Degasser; stationary phase: phenomenex Synergi 2μ Hydro-RP 20×4.0 mm column, mobile phase: A=0.1% formic acid (FA) in water, B=0.1% FA in acetonitrile. Injection volume of 5 μL by CTC Analytical PAL System. Flow is 1 mL/minute. Gradient is 10% B to 90% B in 3 minutes and 90% B to 100% B in 2 minutes. Auxiliary detectors are: Hewlett Packard 1100 Series UV detector, wavelength=220 nm and Sedere SEDEX 75 Evaporative Light Scattering (ELS) detector temperature=46° C., Nitrogen pressure=4 bar.

$^1$H Nuclear Magnetic Resonance Spectra (NMR)

300 MHz $^1$H NMR is recorded at ambient temperature using a Varian Mercury (300 MHz) spectrometer with an ASW 5 mm probe. In the NMR chemical shifts (δ) are expressed ppm relative to tetramethylsilane. Chemical shifts values are indicated in parts per million (ppm) with reference to tetramethylsilane (TMS) as the internal standard.

X-Ray Powder Diffractometry (XRPD)

XRPD is performed on a Siemens-Bruker D5000 diffractometer, using the parafocusing Bragg-Brentano (theta—two-theta)—type geometry. The dihydrogen phosphate salt is deposited on a single-crystal silicon wafer, cut according to the (510) crystallographic orientation. Copper K-alpha radiation (1.54056 angstroms) that is emitted from a copper anti-cathode tube (45 kV/40 mA) is used as the x-ray source, with Cu K-beta radiation being filtered out using a reflected beam monochromator. A scintillation counter is used for detection. A divergence slit of 0.6 mm, an anti-scatter slit of 0.6 mm, a monochromator slit of 0.1 mm, and detector slit of 0.6 mm are used. The diffraction pattern is obtained using the following conditions: 2 to 40 degree scan in angle 2-theta, 1 second count time per step, 0.02 degree step size, under ambient conditions of pressure, temperature, and relative humidity.

Solvation/Hydration State by Thermal Gravimetric Analysis

Thermal analysis is performed using a TA Instruments Model Q-600 Simultaneous Differential Scanning Calorimeter/Thermal Gravimetric Analyzer (DSC/TGA) under a dry nitrogen atmosphere. The TGA temperature is calibrated using an indium standard. The dihydrogen phosphate salt is transferred to an aluminum pan (TA Instruments part number 900793.901). The thermogram is acquired at a linear heating rate of 10° C. per minute.

Differential Scanning Calorimetry (DSC)

DSC is performed using a TA Instruments Model Q-1000 DSC equipped with a refrigerated cooling system under a dry nitrogen atmosphere. The DSC is calibrated using an indium standard. The dihydrogen phosphate salt is transferred to an aluminum pan, and a lid with laser-drilled pinhole (TA Instruments part numbers 900793.901 and 900860.901, respectively) is cold welded to the pan. The DSC thermogram is acquired at a linear heating rate of 10° C. per minute.

Photomicrograph

Photomicrographs are acquired using an Olympus BX-41 microscope equipped with cross polars. The sample is prepared by dispersing it in mineral oil.

Particle Size Distribution

The particle size distribution is measured using a Sympatec HELOS-BF laser diffraction particle size analyzer with the R3 measurement lens, RODOS dry disperser, and laser tuned to 632.8 nm. The system is calibrated using silicon carbide standards. The powder is dispersed using the RODOS dry dispersion attachment with a primary pressure of 3.0 bar and the depression is maximized. The volume based particle size distribution is calculated using the Fraunhofer method by the Sympatec Windox (Version 4.0) software.

Dynamic Water Vapor Sorption (DVS)

The water sorption profile is determined using a SMS Instruments Dynamic Vapor Sorption Analyzer Model DVS-1 or VTI Instruments Model SGA-100 Dynamic Vapor Sorption Analyzer. RH and weight are calibrated using standards. The dihydrogen phosphate salt is loaded and dried at ≦1% RH for 2.5 hours prior to starting the experiment. The RH is stepped from about 0 to 95% RH. The specimen weight is considered constant at each step when percent mass change is less than 0.005% over a 5-minute interval with a minimum absolute equilibration time of 15 minutes.

Fourier Transform-Infrared (FT-IR) Spectroscopy

The FT-IR spectrum is obtained using a Nicolet Magna-IR Spectrometer 55 attached to Nicolet Nic-Plan FT-IR Microscope. A solid sample is analyzed on a KBr disk. The spectrum is obtained after 32 scans from 4000-400 $cm^{-1}$ with 4 $cm^{-1}$ resolution.

The preparation and property of the compound of the invention is described in the following experimental section.

EXAMPLE

Dihydrogen phosphate salt of 2-(3-{6-[2-(2,4-Dichloro-phenyl)-ethylamino]-2-methoxy-pyrimidin-4-yl}-phenyl)-2-methyl-propionic acid Step 1: A solution of 4,6-dichloro-2-methoxypyrimidine (0.7 g), 2,4-dichlorophenethylamine (0.82 g) and sodium bicarbonate (0.88 g) in ethanol (25 mL) is heated at 80° C. for three hours and poured into water (400 mL). The resulting solid is filtered and air dried to afford (6-chloro-2-methoxy-pyrimidin-4-yl)-[2-(2,4-dichloro-phenyl)-ethyl]-amine.

Step 2: To a solution of lithium diisopropylamide in tetrahydrofuran/n-heptane/ethylbenzene (1.8 M, 17 mL) at 0° C. is added a solution of 2-(3-bromo-phenyl)-propionic acid (3 g, 13.9 mmol) in tetrahydrofuran (5 mL) dropwise during 15 minutes. The mixture is stirred for 1 hour, followed by addition of methyl iodide (4.93 g, 34.8 mmol) in tetrahydrofuran (5 mL) dropwise during 10 min. The reaction mixture is stirred for 15 hours, quenched with 2 N HCl, concentrated in vacuo, and diluted with ether (150 mL). The ether layer is washed with 2 N HCl, extracted three times with 2 N NaOH (50 mL). The combined NaOH layers are acidified with 6 N HCl to pH=1 and extracted three times with ether (75 mL). The combined organic layers are washed with brine, dried over sodium sulfate and concentrated to obtain 2-(3-bromo-phenyl)-2-methyl-propionic acid as a solid (3.08 g, 91%), which is used without further purification. LC/MS: 243 (M+H).

Step 3: To a solution of 2-(3-bromo-phenyl)-2-methyl-propionic acid (2.18 mmol) in anhydrous ether (20 mL) is added tert-butyl lithium (1.7 M in pentane, 5.4 mL, 9.16 mmol) dropwise at −78° C. and this mixture is stirred for 30 minutes treated with tributyl borate (2.34 mL, 8.72 mmol). The reaction mixture is allowed to warm up to room temperature, stirred for 15 hours, diluted with ether, and quenched with 1 M $H_3PO_4$. After stirring for 30 minutes the ether layer is separated and extracted three times with 2 N NaOH (20 mL). The combined NaOH extracts are acidified with 6 N HCl to pH=1 and extracted three times with ether (50 mL). The combined organic extracts are washed with brine, dried over sodium sulfate and concentrated to afford 3-(1-carboxy-1-methyl-ethyl)-phenyl boronic acid, which is used without further purification. MS: 209 (M+H).

Step 4: A solution of (6-chloro-2-methoxy-pyrimidin-4-yl)-[2-(2,4-dichloro-phenyl)-ethyl]-amine (0.51 mmol) and 3-(1-carboxy-1-methyl-ethyl)-phenyl boronic acid (0.61 mmol) in acetonitrile (2.5 mL) and aqueous sodium carbonate solution (0.4 M, 2.5 mL) is degassed with nitrogen for 5 minutes before addition of tetrakistriphenylphosphine palladium (0) (29.5 mg, 5 mol %). The reaction vessel is sealed and heated under microwave to 130° C. for 30 minutes. To the reaction mixture is added 2 mL of water, the pH is adjusted to about 7 using 2 N aqueous HCl and this mixture is extracted three times with ethyl acetate (30 mL). The combined extracts are washed with brine, dried over sodium sulfate and concentrated. The residue is subjected to silica gel chromatography to afford 2-(3-{6-[2-(2,4-dichloro-phenyl)-ethylamino]-2-methoxy-pyrimidin-4-yl}-phenyl)-2-methyl-propionic acid as a solid (205 mg, 75%). LC/MS: $R_T$=2.39 minutes, MS: 460 (M+H); $^1$H NMR [300 MHz, $(CD_3)_2SO$]: δ 12.38 (1H, s), 7.36-8.00 (7H, m), 6.58 (1H, s), 3.84 (3H, s), 3.58 (2H, m), 2.98 (2H, m), 1.54 (6H, s).

Step 5: Phosphoric acid (3.21 mL, 1.49 N aqueous solution) is added to a solution of 2-(3-{6-[2-(2,4-dichloro-phenyl)-ethylamino]-2-methoxy-pyrimidin-4-yl}-phenyl)-2-methyl-propionic acid (2.1 g, 4.56 mmol) in tetrahydrofuran (45 mL) and the mixture is stirred for 10 minutes. Water is added drop-wise in intervals until the mixture turned into clear solution, and stirring is continued for 1.5 hours at room temperature. The mixture is concentrated in vacuo, and the residue is recrystallized from acetone to afford the dihydrogen phosphate salt of 2-(3-{6-[2-(2,4-dichloro-phenyl)-ethylamino]-2-methoxy-pyrimidin-4-yl}-phenyl)-2-methyl-propionic acid as a powder (2.4 g, 94%). LCMS: $R_T$=2.41 minutes; MS: 462 (M+H); $^1$H NMR [300 MHz, $(CD_3SO)_2SO$]: δ 7.95 (1H, b), 7.8 (1H, b), 7.6 (2H, b), 7.45 (2H, d, J=2 Hz), 7.35 (2H, s), 6.55 (1H, s), 3.85 (3H, s), 3.55 (2H, b), 2.95 (2H, t, J=2 Hz), 1.5 (6H, s).

Pharmacological Testing

The inhibitory effects of the compound according to the invention are assessed in a human DP functional assay. A cAMP assay is employed using the human cell line LS174T, which expresses the endogenous DP receptor. The protocol is similar to that described previously (Wright D H, Ford-Hutchinson A W, Chadee K, Metters K M, The human prostanoid DP receptor stimulates mucin secretion in LS174T cells, *Br J Pharmacol.* 131(8):1537-45 (2000)).

Protocol for SPA cAMP Assay in Human LS174 T Cells

Materials

PGD2 (Cayman Chemical Cat#12010)

IBMX (Sigma Cat# 5879)

cAMP SPA direct screening assay system (Amersham code RPA 559)

96-well cell plates (Wallac Cat# 1450-516)

Wallac 1450 Microplate Trilux scintillation counter (PerkinElmer)

Plate sealers

Eppendorf tubes

Dulbecco's Phosphate-Buffered Saline (PBS) (Invitrogen Cat#14040-133)

Distilled water

Vortex

Magnetic stirrer and stirrer bars

Reagent Preparation:

All reagents should be allowed to equilibrate to room temperature before reconstitution.

1× Assay Buffer

Transfer the contents of the bottle to a 500 mL graduated cylinder by repeated washing with distilled water. Adjust the final volume to 500 mL with distilled water and mix thoroughly.

Lysis Reagent 1 & 2

Dissolve each of the lysis reagents 1 and 2 in 200 mL assay buffer respectively. Leave at room temperature for 20 minutes to dissolve.

SPA Anti-rabbit Beads

Add 30 mL of lysis buffer 2 to the bottle. Gently shake the bottle for 5 minutes.

Antiserum

Add 15 mL of lysis buffer 2 to each vial, and gently mix until the contents are completely dissolved.

Tracer ($I^{125}$-cAMP)

Add 14 mL lysis buffer 2 to each vial and gently mix until the contents are completely dissolved.

Preparation of Immunoreagent
1) Add equal volumes of tracer, antiserum and SPA anti-rabbit reagent to a bottle, ensuring that a sufficient volume of this mixture is prepared for the desired number of wells (150 µL/well).
2) Mix thoroughly.
3) This immunoreagent solution should be freshly prepared before each assay and not re-used.

Standard
1) Add 1 mL lysis buffer 1 and gently mix until contents are completely dissolved.
2) The final solution contains cAMP at a concentration of 512 pmol/mL.
3) Label 7 polypropylene or polystyrene tubes, 0.2 pmol, 0.4 pmol, 0.8 pmol, 1.6 pmol, 3.2 pmol, 6.4 pmol and 12.8 pmol.
4) Pipette 500 µL of lysis buffer 1 into all the tubes.
5) Into the 12.8 pmol tube pipette 500 µL of stock standard (512 pmol/mL) and mix thoroughly. Transfer 500 µL from 12.8 pmol tube to the 6.4 pmol tube and mix thoroughly. Repeat this doubling dilution successively with the remaining tubes.
6) 50 µL aliquots in duplicate from each serial dilution and the stock standard will give rise to 8 standard levels of cAMP ranging from 0.2-25.6 pmol standard Compound Dilution Buffer Add 50 µL of 1 mM IBMX into 100 mL PBS to make a final concentration of 100 µM and sonicate at 30° C. for 20 minutes.

PGD2 Preparation

Dissolve 1 mg PGD2 (FW, 352.5) in 284 µL DMSO to make 10 mM stock solution and store at 20° C. Before each assay, it is freshly prepared. Add 3 µL of 10 mM stock solution to 20 mL DMSO, mix it thoroughly, and transfer 10 mL to 40 mL PBS.

Compound Dilution

Several batches of the compound of the invention are tested in a 96 well plate. Each batch of the compound occupies one row of the 96 well plate.

Compound dilution is carried out in Biomex 2000 (Beckman) using Method 1_cAMP DP 11 points.

5 µL of each compound from the 10 mM stock compound plates is transferred to the wells of a 96-well plate respectively as below.

|   | 1 | 2 | 3 | 4 | 5 | 6 | 7 | 8 | 9 | 10 | 11 | 12 |
|---|---|---|---|---|---|---|---|---|---|----|----|----|
| A | 1 | | | | | | | | | | | |
| B | 2 | | | | | | | | | | | |
| C | 3 | | | | | | | | | | | |
| D | 4 | | | | | | | | | | | |
| E | 5 | | | | | | | | | | | |
| F | 6 | | | | | | | | | | | |
| G | 7 | | | | | | | | | | | |
| H | reference | | | | | | | | | | | |

Fill the plate with 45 µL of DMSO except column 7 is filled with 28 µL DMSO. Pipette column 1 thoroughly, and transfer 12 µL into column 7 parallel. Perform 1:10 serial dilution from column 1 to column 6 and from column 7 to column 11 by transfer 5 µL to 45 µL DMSO to make following concentrations:

| First plate | Final concentration |
|---|---|
| Column 12 | 0 |
| Column 11 | 0.03 µM |
| Column 10 | 0.3 µM |
| Column 9 | 3 µM |
| Column 8 | 0.03 mM |
| Column 7 | 0.3 mM |
| Column 6 | 0.01 µM |
| Column 5 | 0.1 µM |
| Column 4 | 1 µM |
| Column 3 | 0.01 mM |
| Column 2 | 0.1 mM |
| Column 1 | 1 mM |

Fill a new 96-well plate with 247.5 µL of compound dilution buffer. Transfer 2.5 µL of serially diluted compounds from above plate to the new plate (1:100 dilution) as following:

| First plate | Second plate | Final concentration |
|---|---|---|
| Column 12 | Column 1 | 0 |
| Column 6 | Column 2 | 0.1 nM |
| Column 11 | Column 3 | 0.3 nM |
| Column 5 | Column 4 | 1 nM |
| Column 10 | Column 5 | 3 nM |
| Column 4 | Column 6 | 0.01 µM |
| Column 9 | Column 7 | 0.03 µM |
| Column 3 | Column 8 | 0.1 µM |
| Column 8 | Column 9 | 0.3 µM |
| Column 2 | Column 10 | 1 µM |
| Column 7 | Column 11 | 3 µM |
| Column 1 | Column 12 | 10 µM |

Cell Growth
1. LS174T are always grown in MEM (ATCC Cat# 30-2003), 10% FBS (ATCC Cat# 30-2020) and additional 2 mM L-glutamine, at 37° C. and 5% $CO_2$.
2. Warm 0.05% Trypsin and Versine (Invitrogen Cat# 25300-054) at 37° C. water bath.
3. Remove growth medium from cells. Cells in T165 flask are washed twice with 4 mL Trypsin followed by incubation at 37° C. and 5% $CO_2$ for 3 minutes.
4. Add 10 mL of medium and pipette thoroughly to separate the cells and count the cells.
5. Bring the cell density to $2.25 \times 10^5$ cells/ml and seed 200 µL cells/well (45,000 cells/well) in 96-well plates 1 day before the assay.

Assay Procedure

Day 1

Seed 45,000 cells/well in 200 µL medium in 96-well plates. Incubate the cell plate at 37° C., 5% $CO_2$ and 95% humidity overnight.

Day 2
1. Perform compound dilution.
2. Prepare assay buffer, lysis buffer 1 & 2, $PGD_2$ and standard.
3. Aspirate media from the cells and add 100 µL of compound solution using Zymark Sciclone-ALH/FD protocol cAMP DP.
4. Incubate the cells at 37° C., 5% $CO_2$ and 95% humidity for 15 minutes.
5. Add 5 µL of 300 nM PGD2 (20×15 nM final concentration) into each well using Zymark protocol cAMP DP PGD2, and incubate the cells at 37° C., 5% $CO_2$ and 95% humidity for additional 15 minutes.
6. Aspirate media from the cells and add 50 µL of lysis buffer 1 using Zymark protocol cAMP DP lysis, and incubate at room temperature with shaking for 30 minutes.
7. Add 150 µL immunoreagent to all wells (a total volume of 200 µL/well).
8. Seal the plates and shake for 2 minutes, put into the chamber of the Wallac microtitre plate µ scintillation counter for 16 hours.

Day 3

Count the amount of [$^{125}$I] cAMP for 2 minutes in 1450 Trilux scintillation counter.

Data Processing

Set up Standard Curve of cAMP Versus CPM.

TABLE 1

Typical assay data for standard

| cAMP (pmol/mL) | CPM | | Average CPM |
|---|---|---|---|
| 0.2 | 5725 | 5769 | 5530 |
| 0.4 | 5367 | 5259 | 6317 |
| 0.8 | 4695 | 4796 | 6507 |
| 1.6 | 4251 | 4178 | 6581 |
| 3.2 | 3434 | 3429 | 6601 |
| 6.4 | 2758 | 2716 | 6711 |
| 12.8 | 2094 | 2054 | 6680 |
| 25.6 | 1531 | 1573 | 6653 |

The cAMP concentrations (pmol/mL) of unknown samples are calculated from a standard curve of cAMP versus CPM % inhibition is calculated using the following formula:

$$\% \text{ Inhibition} = \frac{(\text{pmol of control} - \text{pmol of sample}) \times 100}{\text{pmol of control (cells} + \text{PGD2 only)}}$$

Results

The dihydrogen phosphate salt produces 50% inhibition in the SPA cAMP assay in human LS174 T cells at a concentration of 0.3 nanomolar.

The dihydrogen phosphate salt has increased aqueous solubility over the free form and the hydrochloride salt. The following chart lists the solubilities of the free form, the hydrochloride salt and the dihydrogen phosphate salt at 25° C. in phosphate buffer (PBS pH 7.4, a mixture of 19% of a 0.1M monobasic sodium phosphate solution and 81% of a 0.1M dibasic sodium phosphate solution) and the solubilities of the free form and the dihydrogen phosphate salt 37° C. in a simulated intestinal fluid under fasted conditions ("FaSSIF", prepared according to Dressman J. B., Amidon G. L., Reppas C. and Shah V. P., Dissolution testing as a prognostic tool for oral drug absorption: immediate release dosage forms, *Pharmaceutical Research:* 1998, Vol. 15, No. 1, 11-22).

| | Solubility (PBS pH 7.4, 25° C., µg/mL) | Solubility in FaSSIF (37° C., ug/mL) |
|---|---|---|
| Free form | <1 | 14 |
| Hydrochloride salt | 5 | |
| Dihydrogen phosphate salt | 15 | 266 |

Figure 8:
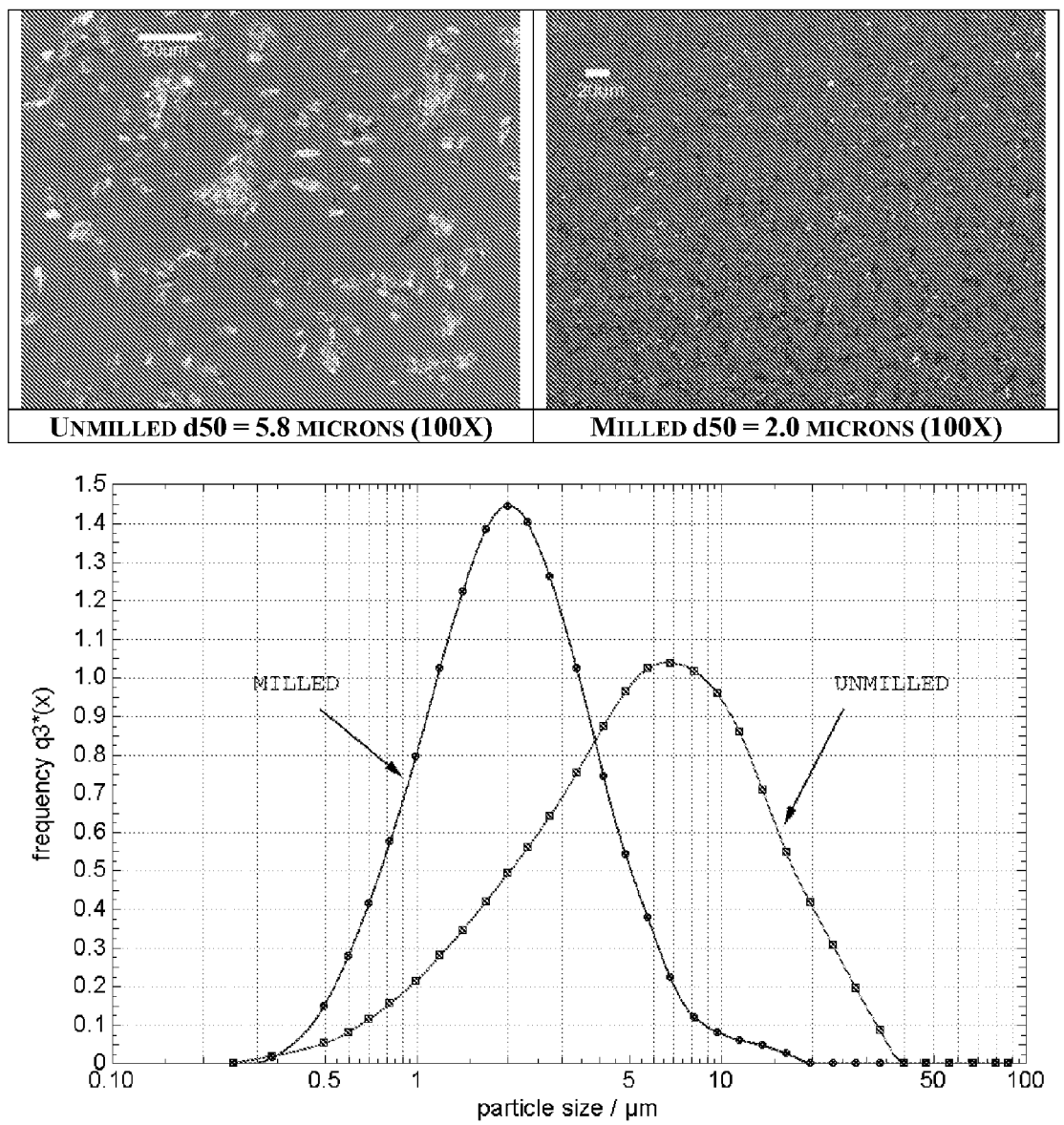
FIG. 8 shows photomicrographs pre- and post-milling of the dihydrogen phosphate salt and the quantitative particle size distribution, showing a good reduction in particle size with no change in physicochemical properties. The photomicrograph post-milling of the dihydrogen phosphate salt shows a well-micronized, crystalline material with no particles greater than 10 microns in length during a search of ~30 fields at 100× magnification. The particle size distribution of the micronized dihydrogen phosphate salt is determined to be a single mode curve. The median [x(50)] is 2.0 microns and 90% of the particles are 4.7 microns or less. The micronization process reduces both the median (5.8 microns before) and the x(90) size (~16 microns before). The XRPD, i.e., peak intensities, location (d-spacing) and resolution, of the dihydrogen phosphate salt, before and after micronization, are the same.
Figure 9:
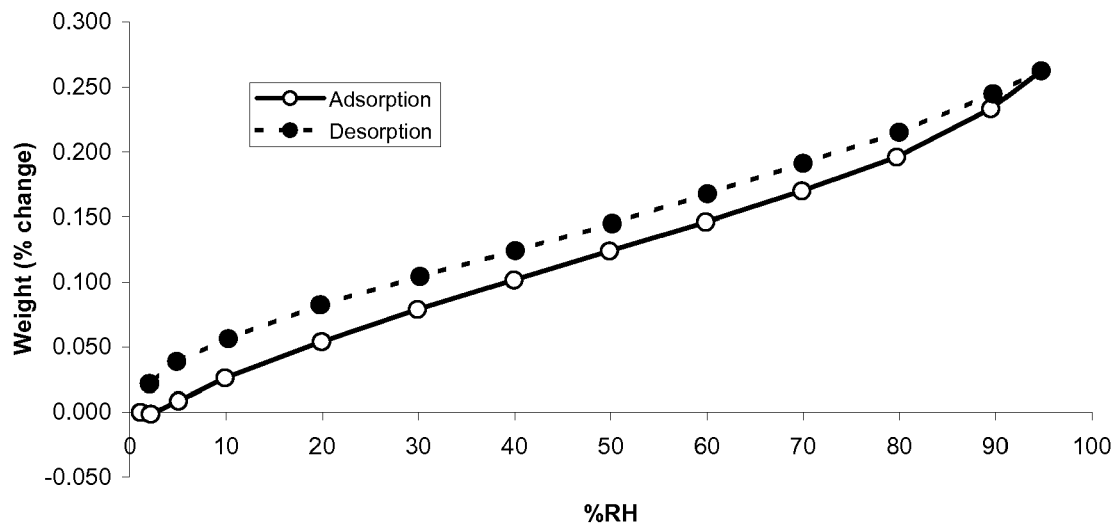
FIG. 9 is a DVS Hygroscopicity Isotherm of the dihydrogen phosphate salt after micronization showing no amorphization.
Figure 10:
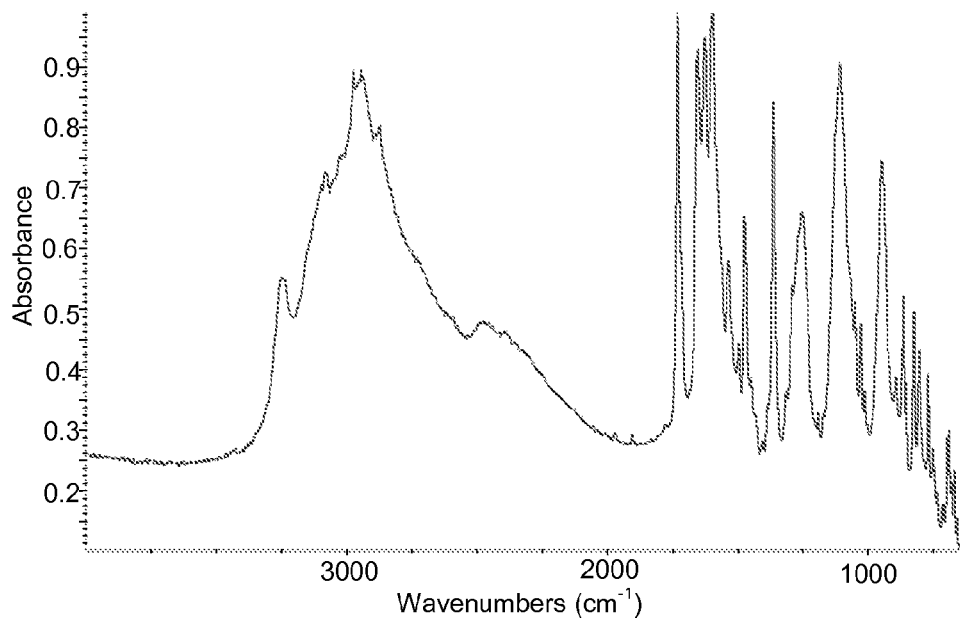
FIG. 10 shows a Fourier Transform-Infrared (FT-IR) spectrum for the dihydrogen phosphate salt and the corresponding Table of FT-IR peaks.

The dihydrogen phosphate salt also has unexpected properties that are useful for large-scale manufacturing and pharmaceutical formulation. First, the dihydrogen phosphate salt has very good crystallinity. The XRPD of the dihydrogen phosphate salt shown in FIG. 1 contains peaks with moderate intensities and resolution. The absence of a halo in the mid two-theta region suggests little, if any amorphous phase. In addition, photomicrographs pre- and post-milling of the dihydrogen phosphate salt shown in FIG. 8 evidence a good reduction in particle size with no change in physicochemical properties.

Figure 11:
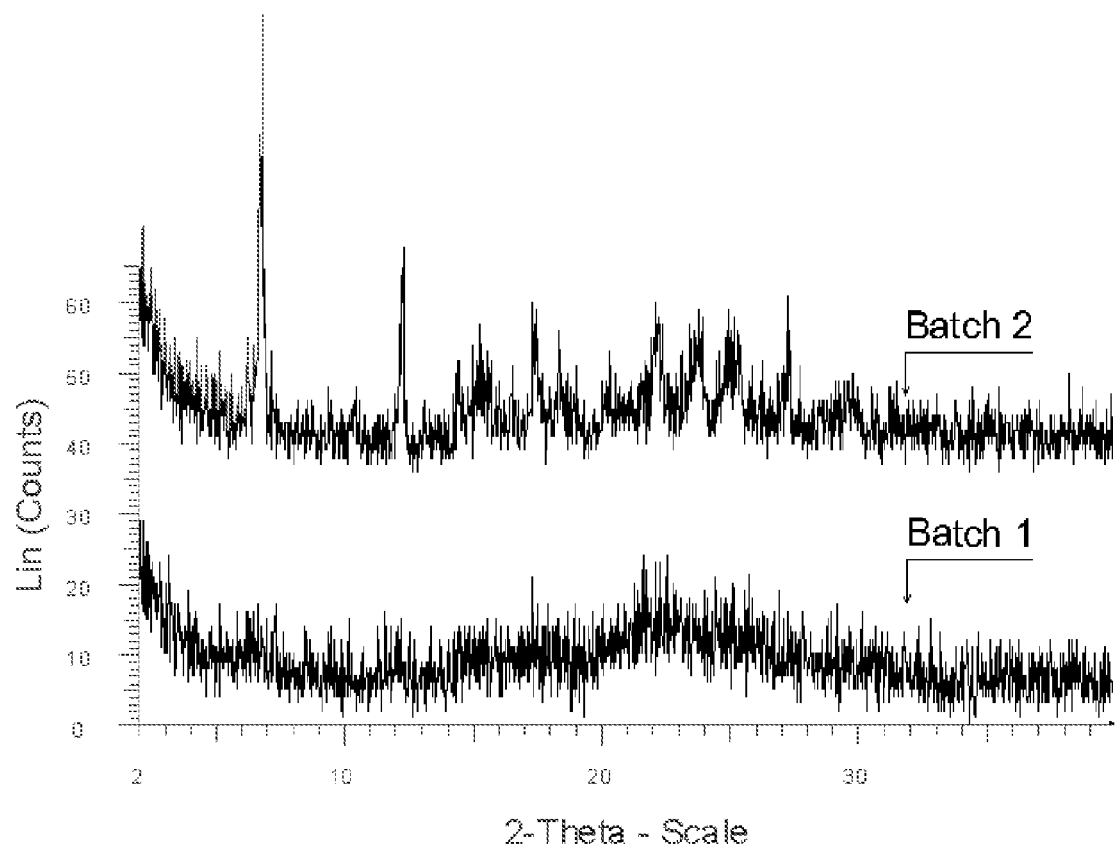
FIG. 11 shows an overlay of the XRPD patterns for two separate preparations, Batch 1 and Batch 2, of the sodium salt. Batch 1 of the sodium salt is recrystallized from ethanol:ethyl acetate. The Batch 2 of the sodium salt is recrystallized from methanol:ethyl acetate.

The sodium salt, however, has low crystallinity. As shown in FIG. 11, the XRPD of Batch 2 of the sodium salt contains broad peaks with low intensities, indicating low crystallinity. The XRPD of Batch 1 of the sodium salt shows that the material is mostly amorphous. In addition, the presence of a halo in the mid two-theta region in the XRPD of both batches suggests very poor crystallinity of the material.

Figure 12:
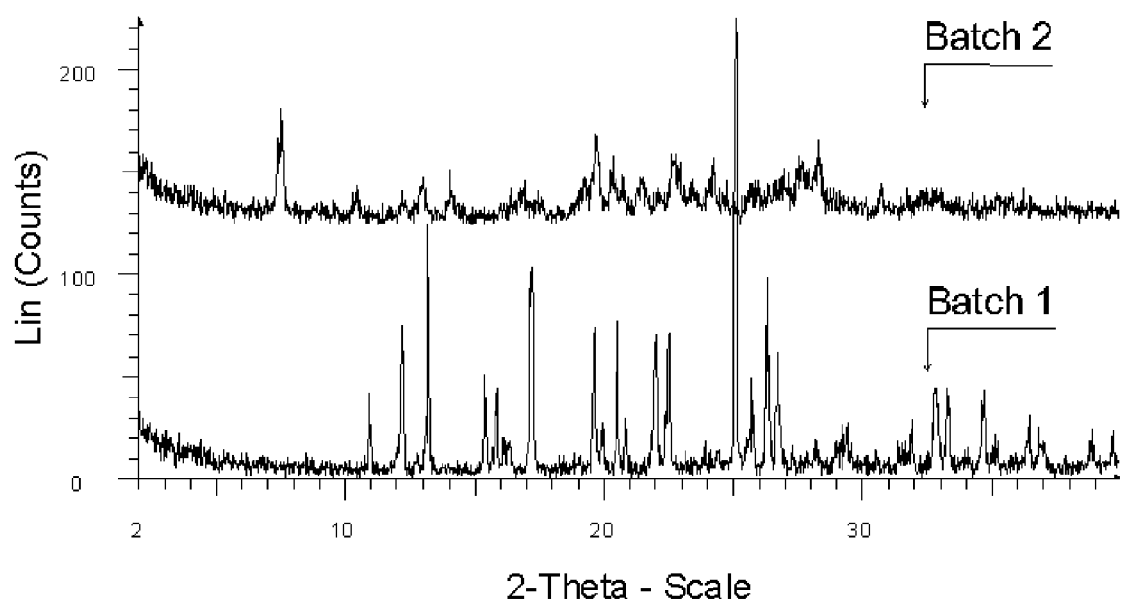
FIG. 12 shows an overlay of the XRPD patterns for two separate preparations, Batch 1 and Batch 2, of the hydrochloride salt recrystallized from acetone.

Furthermore, the dihydrogen phosphate salt presently has been shown to exist only in one polymorphic form. The hydrochloride salt, however, presently has been shown to exist in three polymorphic forms, which might be subject to interconversion under certain conditions. One of the polymorphic forms of the hydrochloride salt, Batch 2 in FIG. 12, has low crystallinity as the XRPD contains broad peaks with low intensities. Another one of the polymorphic forms of the hydrochloride salt, Batch 1 in FIG. 12, has good crystallinity.

We claim:

1. A compound of Formula (III)

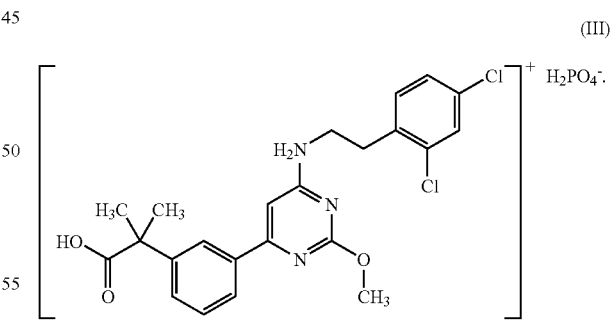

(III)

2. A pharmaceutical composition comprising a pharmaceutically effective amount of the compound according to claim 1 in admixture with a pharmaceutically acceptable carrier.

3. A method for treating bronchial asthma in a patient in need thereof, comprising administering to the patient a pharmaceutically effective amount of the compound according to claim 1.

* * * * *